US006020205A

United States Patent [19]
Vojdani

[11] Patent Number: 6,020,205
[45] Date of Patent: Feb. 1, 2000

[54] DETERMINATION OF INTRACELLULAR ANTIOXIDANT LEVELS

[75] Inventor: Aristo Vojdani, Los Angeles, Calif.

[73] Assignee: Immunosciences Lab, Inc., Beverly Hills, Calif.

[21] Appl. No.: 09/058,718

[22] Filed: Apr. 10, 1998

[51] Int. Cl.[7] .......... G01N 33/00

[52] U.S. Cl. .......... 436/87; 436/63; 436/86; 436/93; 436/99; 436/161; 436/813; 435/2

[58] Field of Search .......... 436/63, 86, 87, 436/93, 99, 161, 174, 177, 813; 435/2

[56] References Cited

U.S. PATENT DOCUMENTS

| | | | |
|---|---|---|---|
| 5,607,974 | 3/1997 | Droge et al. | 514/562 |
| 5,830,455 | 11/1998 | Valtuena et al. | 424/85.4 |
| 5,843,785 | 12/1998 | Herzenberg et al. | 436/86 |

OTHER PUBLICATIONS

Eck et al. *Biological Chemistry—Hoppe—Seyler*, vol. 370, pp. 101–108, Feb. 1989.

Fotouhi et al. *American Journal of Clinical Nutrition*, vol. 63, pp. 553–558, 1996.

Baker et alt., Our Experiences with Vitamin Malabsorption: An Overview, *Surv. Dig. Dis.* 1:203–216 (1983).

Block, Gladys, Vitamin C and cancer prevention: the epidemiologic evidence, *Am. J. Clin. Nutr.* 53:270S–282S (1991).

Levine, et al., Vitamin C pharmacokinetics in healthy volunteers: Evidence for a recommended dietary allowance, *Proc. Natl. Acad. Sci. USA*, 93:3704–3709 (1996).

Lykkesfeldt, et al., Determination of Ascorbic Acid and Dehydroascorbic Acid in Plasma by High–Performance Liquid Chromatorgraphy with Coulometric Detection—Are They Reliable Biomarkers of Oxidative Stress, *Analytical Biochemistry*, 229:329–335 (1995).

Patterson, et al., Vitamin supplements and cancer risk: the epidemiologic evidence, *Cancer Causes and Control*, 8:786–802 (1997).

Rose, et al, Analysis of water–soluble antioxidants by high–pressure liquid chromatography, *Biochem. J.* 306:101–105 (1995).

Shamberger, Raymond J., Antioxidants and Cancer, *vol. II* 53–58 (1983).

Sinha et al., Serum Ascorbic Acid Stability Over An Extended Period: Relevance to Epidemiological Studies; *Nutrition Research*, 17(9)1409–1415 (1997).

Stahl, et al., Cis–trans Isomers of Lycopene and β–Carotene in Human Serum and Tissues, *Arch. Biochem. Biophys.* 294(1):173–177 1992).

Zhu, et al., Vitamin E concentration in breast adipose tissue of breast cancer patients (Kuopio, Finland), *Cancer Causes and Control* 7:591–595 (1996).

*Primary Examiner*—Maureen M. Wallenhorst
*Attorney, Agent, or Firm*—Knobbe, Martens, Olson & Bear, LLP

[57] ABSTRACT

A method of determining intracellular levels of water-soluble and fat-soluble antioxidants. Peripheral blood mononuclear cell lysates are prepared from an individual and analyzed by HPLC, either directly or after extraction with organic solvents to extract fat-soluble antioxidants. The levels of antioxidants are compared to normal levels as an indication of the overall oxidative health of the individual.

7 Claims, 5 Drawing Sheets

DETERMINATION OF INTRACELLULAR ANTIOXIDANT LEVELS

FIELD OF THE INVENTION

The present invention relates to a method for determining whether an individual is at risk for developing cancer. More particularly, the invention relates to the determination of intracellular levels of water-soluble and fat-soluble antioxidants.

BACKGROUND OF THE INVENTION

It is well known that both synthetic and natural antioxidants inhibit carcinogenesis and mutagenesis (Shamberger, Volume II, pp. 53–58; Block et al., *Am J. Clin. Nutr.* 53:270S–282S). Natural antioxidants include ascorbic acid (vitamin C), selenium, oxidized glutathione (GSSG), and reduced glutathione (GSH), which are water-soluble, and the fat-soluble antioxidants α-carotene, β-carotene (precursor of vitamin A), α-tocopherol (vitamin E), γ-tocopherol, lycopene and coenzyme $Q_{10}$. These antioxidants can be obtained from various food sources, or can be taken as nutritional supplements. Vitamin deficiencies (hypovitaminosis) underlie many human diseases or, conversely, many diseases lead to vitamin deficiencies (Banker et al., *Survey of Digestive Diseases* 1:203–216, 1983). Hypovitaminosis may result from decreased intake, absorption defects, decreases storage avidity and excessive conversion to metabolites (metabolic destruction).

Randomized clinical trials of vitamin supplementation have shown significant protective effects of α-tocopherol against prostate cancer, mixtures of retinol/zinc and β-carotene/α-tocopherol/selenium against stomach cancer; and selenium against total, lung and prostate cancers (*Cancer Causes and Control*, 8:786–8023 1997).

Antioxidant levels in plasma and tissues have been extensively quantitated. Rose et al. (*Biochem. J.* 306:101–105, 1995) quantified three water soluble antioxidants, ascorbic acid, reduced glutathione and uric acid, from rat tissue homogenates using high-pressure liquid chromatography. Sinha et al. (*Nutrition Res.* 17:9, 1409–1415, 1997) examined the stability of ascorbic acid in serum by spectrophotometric determination using 2,4-dinitrophenylhydrazine. Lykkesfeldt et al. (*Anal. Biochem.* 229:329–335, 1995) determined plasma ascorbic acid levels using HPLC with coulometric detection as a biomarker of oxidative stress. Comstock et al. compared blood antioxidant levels and correlated these levels with the incidence of lung cancer in 258 patients. Among the total group of 258 cases and 515 controls, serum/plasma concentrations were significantly lower among cases than controls for cryptoxanthin, β-carotene, and lutein/zeaxanthin. Modest differences in a protective direction were noted for α-carotene and ascorbic acid. Stahl et al. (*Arch. Biochem. Biophys.* 294:173–177, 1992) measured β-carotene and lycopene levels in human serum and tissues. Zhu et al. (*Cancer Causes and Control* 7:591–595, 1996) analyzed vitamin E levels in breast adipose tissue of breast cancer patients and determined that levels were significantly lower in patients with breast cancer versus benign breast disease. Levine et al. (*Proc. Natl. Acad. Sci. U.S.A.*, 93:3704–3709, 1996) studied steady state plasma and tissue concentrations of vitamin C at seven daily doses from 30 to 2,500 mg. For determination of the Recommended Dietary Allowance (RDA) for Vitamin C, it was concluded that the current RDA of 60 mg daily should be increased to 200–400 mg daily.

The measurement of endogenous antioxidants is of importance because the values obtained may be an indicator of future health. Most methods of determining antioxidant levels focus on serum and adipose tissue. However, because serum levels reflect only those antioxidants which cannot be absorbed, this is not an accurate indication of intracellular levels. Because it is difficult to obtain tissue from an individual for assaying antioxidant levels, this is also not a particularly desirable method. Thus, there is a need for an accurate, convenient method for determining intracellular antioxidant levels to assess the overall oxidative health of an individual and to rule out absorption defects. The present invention provides such a method.

SUMMARY OF THE INVENTION

One embodiment of the present invention is a method for determining whether an individual requires an increase in precautionary measures to lower the risk of developing cancer, comprising the steps of obtaining a median control level of one or more antioxidants present in a human; isolating a complete peripheral blood mononuclear cell (PBMC) fraction from the individual; determining the level of the one or more antioxidants present in the complete PBMC fraction by high pressure liquid chromatography (HPLC); and comparing the level of the one or more antioxidants to the control level of the one or more antioxidants, wherein a decrease in the level of said one or more antioxidants compared to the control levels indicates that precautionary measures are required. Preferably, the one or more antioxidants are water-soluble. Alternatively, the one or more antioxidants are fat-soluble. In another aspect of this preferred embodiment, the antioxidants are a combination of water-soluble and fat-soluble antioxidants. Advantageously, the determining step comprises HPLC. Preferably, the one or more water-soluble antioxidants are ascorbic acid, oxidized glutathione, reduced glutathione, cysteine or uric acid. Advantageously, the one or more fat-soluble antioxidants are α-carotene, β-carotene, lycopene, α-tocopherol, γ-tocopherol, retinol, lutein, zeaxanthin, cryptoxanthin or coenzyme $Q_{10}$.

DETAILED DESCRIPTION OF THE PREFERRED EMBODIMENTS

Figure 1:
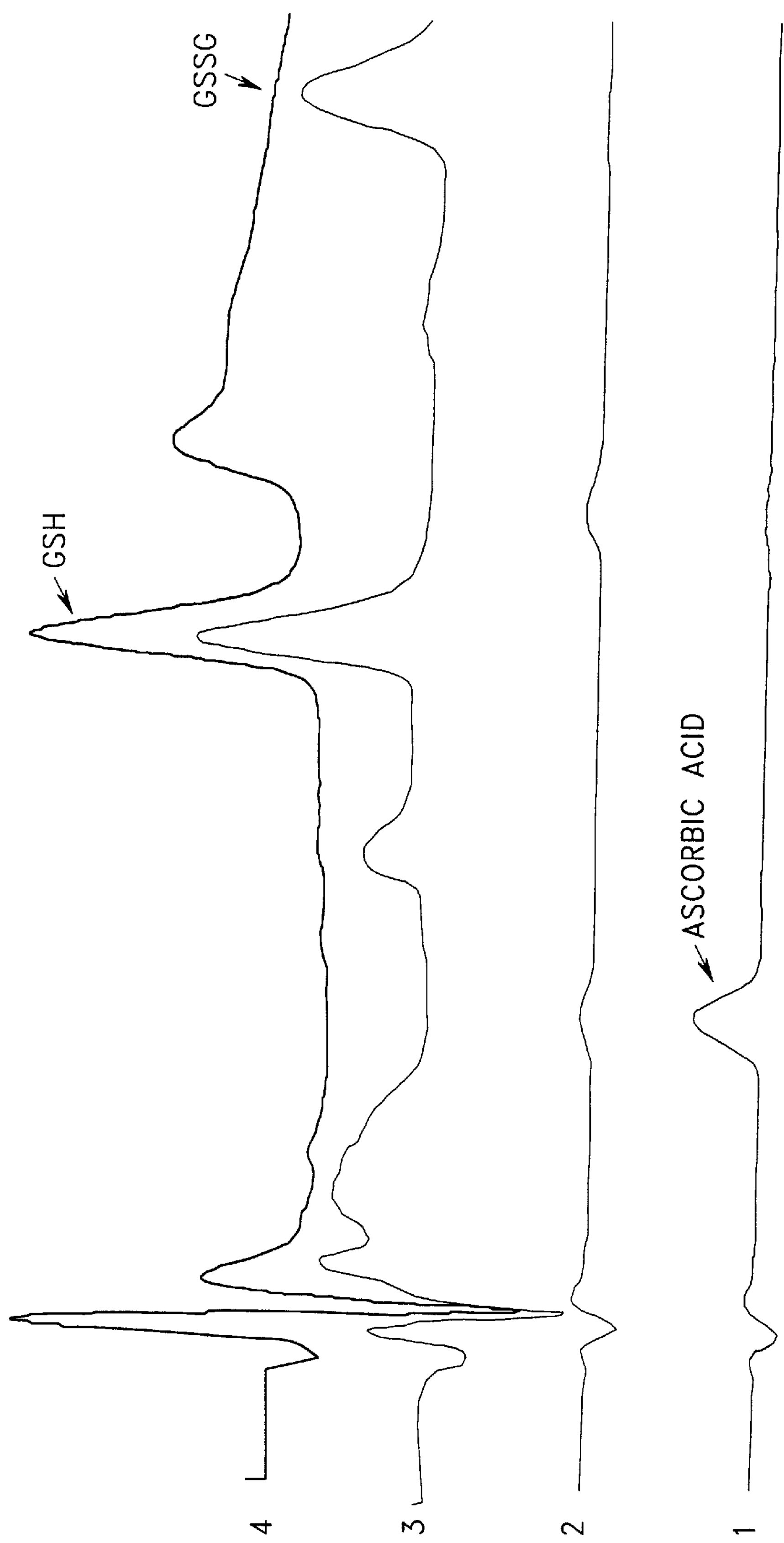
FIG. 1 is an chromatograrn showing basal levels of ascorbic acid, oxidized glutathione and reduced glutathione in PBMCs from an individual as measured by HPLC.

The present invention provides a method for determining the intracellular levels of water-soluble and fat-soluble antioxidants as an indication of overall oxidative health. Although plasma levels of various antioxidants have been previously determined, these do not accurately reflect intracellular antioxidant levels due to efficiency of cellular antioxidant uptake and other factors. Thus, a more accurate reflection of the overall oxidative health of an individual is the intracellular level of antioxidants because these compounds exert their beneficial effects, particularly inhibition of free radical-induced oxidative damage, within the cell. In addition, intracellular PBMC antioxidant levels reflect tissue levels of these compounds.

The present method can be used to determine whether an individual requires an increase in precautionary measures to lower the risk of developing cancer. Such measures include the increased intake of one or more antioxidants which are determined to be low compared to a group of healthy individuals, increased exercise, a change in environment, decreased dietary fat intake and decreased exposure to chemicals.

The present method involves analysis of antioxidant levels in a complete peripheral blood mononuclear cells (PBMC) fraction by high performance liquid chromatography (HPLC). PBMC are isolated from blood using conventional Ficoll-Hypaque density gradient centrifugation. Water-soluble antioxidants analyzed by the present method include, but are not limited to, ascorbic acid (vitamin C), reduced glutathione, oxidized glutathione, cysteine and uric acid. Fat-soluble antioxidants include, but are not limited to, retinol, γ-tocopherol, α-tocopherol, Vitamin K, α-carotene, β-carotene, lycopene, coenzyme $Q_{10}$, lutein, zeaxanthin and cryptoxanthin. Each of these antioxidants has a characteristic retention time on an HPLC column and can easily be identified on an HPLC chromatogram by comparing the peaks in a particular sample with calibration standards of each compound. The amount of compound present is determined by integrating across the area of the peak.

If the level of one or more plasma or intracellular antioxidants is determined to be below average for an individual, it is advisable for the individual to increase precautionary measures for reducing the risk of developing cancer. For example, if β-carotene and lycopene levels are low, the individual can either eat more foods which contain high levels of these nutrients or can take vitamin supplements. Normal plasma levels of various antioxidants in healthy individuals are presented in Table 1.

TABLE 1

Normal plasma antioxidant levels

| ANTIOXIDANT | NORMAL LEVELS (ng/ml) |
|---|---|
| GSH | 20,000–40,000 |
| GSSG | 10,000–30,000 |
| ascorbic acid | 5,000–10,000 |
| lutein | 150–300 |
| γ-tocopherol | 1,400–2,000 |
| α-tocopherol | 5,000–15,000 |
| Vitamin K1 | 5–10 |
| Lycopene | 250–400 |
| α-carotene | 80–200 |
| β-carotene | 200–500 |
| coenzyme $Q_{10}$ | 200–500 |
| retinol | 400–600 |

As described in the following examples, PBMC were isolated from healthy individuals, healthy individuals after taking vitamin supplements, and breast cancer patients, and the levels of both fat-soluble and water-soluble antioxidants were determined by HPLC.

EXAMPLE 1

Isolation of PBMC

3×10 ml of blood was drawn and placed in yellow top tubes containing acid citrate dextrose (ACD) (Becton- Dickinson, Palo Alto, Calif.). Peripheral blood mononuclear cells (PBMC) were separated by Ficoll-Hypaque density gradient centrifugation using HISTOPAQUE®-1077 (Sigma Diagnostics, St. Louis, Mo.) according to the manufacturer's instructions. Briefly, 3.0 mL HISTOPAQUE®-1077 was added to a 15 mL conical centrifuge tube and brought to room temperature. Whole blood (3.0 mL) was carefully layered onto the HISTOPAQUE®-1077 and centrifuged at 400×g for 30 minutes at room temperature. The upper layer was aspirated to within 0.5 cm of the opaque interface containing PBMC, and discarded. The opaque interface was transferred into a clean conical centrifuge tube to which 10 mL of phosphate buffered saline (PBS) was added and mixed with gentle aspiration. The sample was centrifuged at 250×g for 10 minutes and the supernatant was aspirated and discarded. The cell pellet was resuspended in 5.0 mL PBS and mixed by gentle aspiration, followed by centrifugation at 250×g for 10 minutes. The aspiration, resuspension and centrifugation steps were repeated, the supernatant was discarded and the cell pellet was resuspended in 200 μl ethanol/BHA for analysis of fat-soluble vitamins or in 200 Ill phosphate buffer for analysis of water-soluble vitamins as described below.

EXAMPLE 2

Analysis of fat-soluble antioxidants from PBMC

For fat-soluble antioxidant analysis, $2\times10^7$ PBMC prepared as described in Example 1 were combined with 200 μl ethanol containing 0.001% butylated hydroxyanisole (BHA) and sonicated for 5 seconds at 20–40% output. The sample was centrifuged at 4,000 rpm for 10 min, and the supernatant was removed and combined with 1 ml hexane. Following addition of hexane, 800 μl supernatant was evaporated to dryness and the resulting residue was dissolved in 200 μl ethanol/BHA, followed by vortexing for 5 minutes. The sample was centrifuged for 10 min at 10,000 rpm and 50 μl of the supernatant was analyzed by HPLC with a coulometric electrode array detector (CoulArray™) manufactured by ESA, Inc. (Chelmsford, Mass.). The CoulArray™ is a coulometric multi-electrode electrochemical detector for HPLC which uses a multi-electrode detector system in which a series of electrochemical cells (up to 16) are set at different potentials to oxidize (or reduce) the compounds that elute from the column. This approach allows for the collection of a number of chromatograms rather than a single chromatogram, and thus allows for the identification of the compound of interest based on the retention time and its oxidation (reduction) characteristics on several traces. It is highly unlikely that two compounds that elute at the same time have a similar oxidation (reduction) profile.

The following HPLC solutions were used: Solution A was prepared with 656 mg sodium acetate in 200 ml deionized water, the pH was adjusted to 4.4 with acetic acid, and 200 ml of this solution was combined with 1800 ml methanol. Solution B was prepared with 2.05 g sodium acetate, 50 ml deionized water, the pH was adjusted to 4.4 with acetic acid, and 40 ml of this solution was combined with 1560 ml methanol and 400 ml butanol. The HPLC column was washed with pure isopropanol. The height of the peaks were compared to calibrated standards and normal serum.

For determination of plasma levels of fat-soluble antioxidants 200 μl of serum, rather than PBMC, was processed as described above.

EXAMPLE 3

Analysis of water-soluble antioxidants from PBMC

For water-soluble antioxidant analysis, $2\times10^7$ PBMC prepared as described in Example 1 were combined with 200 μl phosphate buffer (50 mM $H_3PO_4$, pH 1.8, 0.1 mM EDTA), sonicated for 5 seconds at 20–40% output and centrifuged for 10 minutes using a filter which removes molecules having a molecular weight of greater than 10,000 daltons (GIBCO BRL Life Technologies, Inc., Gaithersburg, Md.). The sample (50 μl) was then injected into the HPLC. The HPLC solution contained 0.2M $KH_2PO_4/H_3PO_4$ or 0.2 M $NaH_2PO_4/H_3PO_4$, 20 ml methanol, 200 mg 1-pentanesulfonic acid, 200 μl microbiocide (ESA, Inc, Chelmsford, Mass.), and optionally 1 g citric acid. The HPLC column was washed with 5% methanol.

For determination of plasma levels of fat-soluble antioxidants 200 μl of serum, rather than PBMC, was processed as described above.

Figure 2:
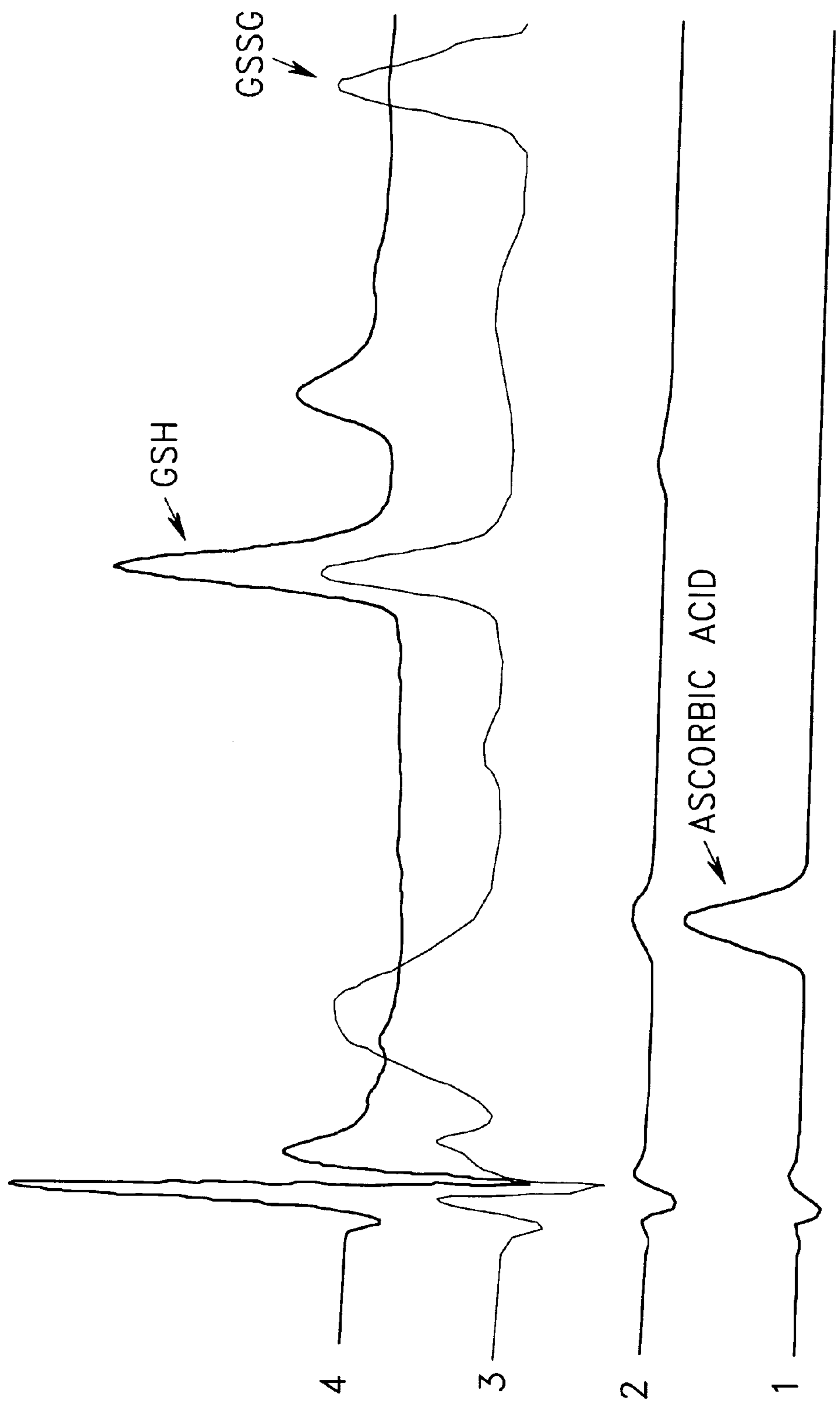
FIG. 2 is a chromatogram showing levels of ascorbic acid, oxidized glutathione and reduced glutathione in PBMC from an individual 20 hours after taking a multivitamin supplement.
Figure 3:
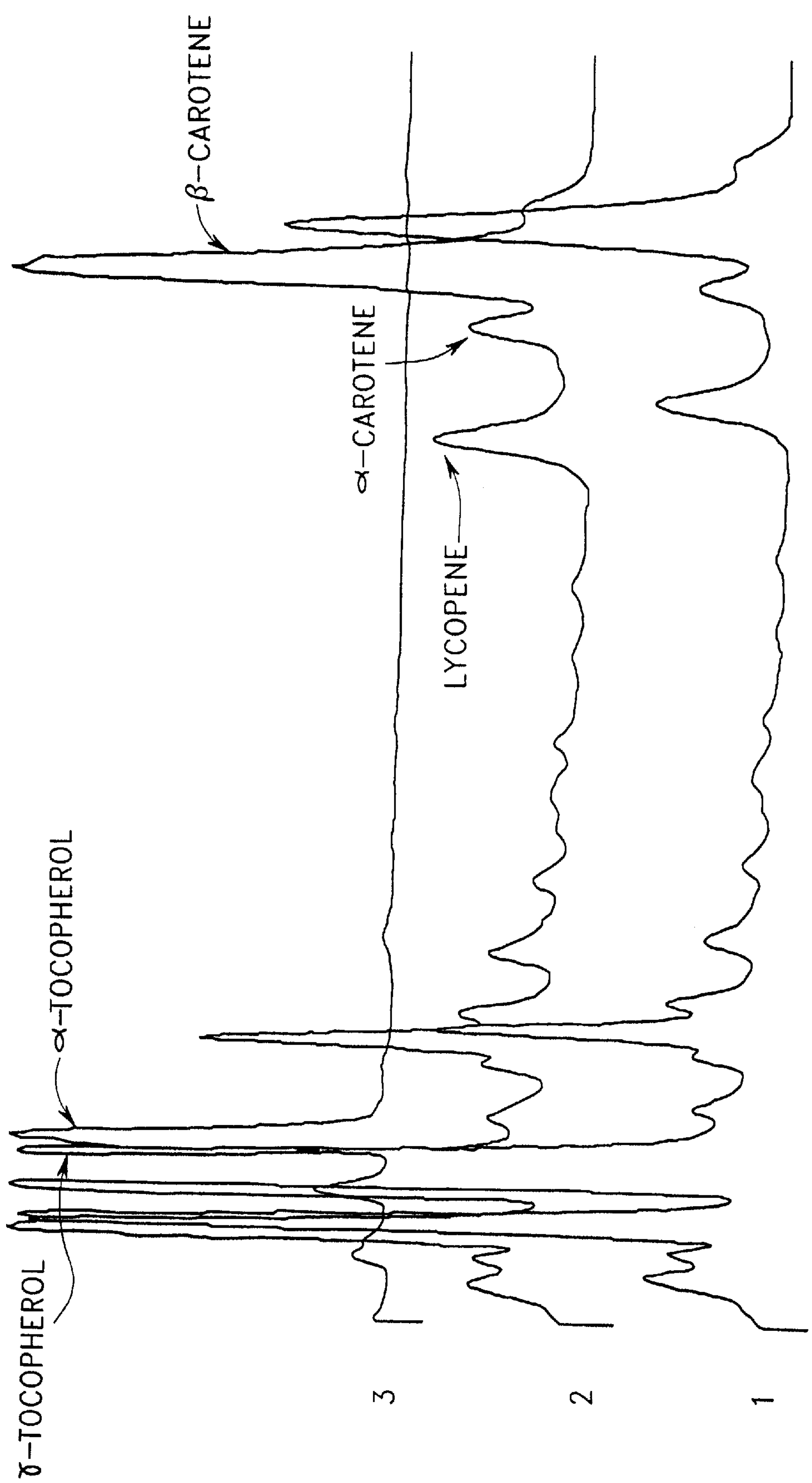
FIG. 3 is a chromatogram showing levels of fat-soluble antioxidants in PBMC from an individual both before (lower line) and 20 hours after (upper line) taking a multivitamin supplement.

PBMC were isolated from healthy individuals, from healthy individuals after taking vitamin supplements, and from breast cancer patients and antioxidant levels were determined by HPLC. As shown in FIGS. 1 and 2, since vitamin supplementation included vitamin C and fat-soluble vitamins, but not glutathione, intracellular levels of ascorbic acid and not glutathione increased significantly 20 hours after vitamin use. Levels of various fat-soluble antioxidants also increased 20 hours after vitamin use (FIG. 3).

Table 2 summarizes the intracellular levels of ascorbic acid, oxidized glutathione and reduced glutathione (in ng/$3\times10^7$ PBMC) in an individual before, 4 hours after and 20 hours after taking a vitamin supplement. This table shows that water-soluble antioxidants (vitamin C) are taken up by cells in a time-dependent manner.

TABLE 2

Intracellular water-soluble antioxidant levels before and after vitamin use
Mean ± SD of 10 healthy control individuals

| ANTIOXIDANT | 0 hours | 4 hours | 20 hours |
|---|---|---|---|
| Ascorbic acid | 5879 ± 1946 | 6247 ± 1862 | 11435 ± 2650 |
| GSSG | 36590 ± 17610 | 35870 ± 19180 | 32780 ± 20100 |
| GSH | 41470 ± 16520 | 42490 ± 17080 | 45940 ± 20360 |

Table 3 summarizes the intracellular levels of fat-soluble antioxidants (in ng/$2\times10^7$ PBMC) in an individual before, 4 hours after and 20 hours after taking a vitamin supplement. As shown in the table, the amount of each antioxidant increased four hours after vitamin use. After 20 hours, intracellular levels began decreasing, with some of them returning to pre-vitamin levels.

TABLE 3

Intracellular fat-soluble antioxidant levels before and after vitamin use
Mean ± SD of 10 healthy control individuals - ng/2 × $10^7$ cells

| ANTIOXIDANT | 0 hours | 4 hours | 20 hours |
|---|---|---|---|
| α-tocopherol | 2986 ± 855 | 4283 ± 1360 | 4128 ± 987 |
| γ-tocopherol | 563 ± 287 | 793 ± 318 | 682 ± 267 |
| lycopene | 116 ± 31 | 217 ± 43 | 184 ± 36 |
| α-carotene | 18 ± 7 | 31 ± 12 | 27 ± 10 |
| β-carotene | 77 ± 26 | 91 ± 33 | 92 ± 21 |
| coenzyme $Q_{10}$ | 206 ± 43 | 281 ± 72 | 229 ± 35 |

Tables 4 and 5 show levels of water-soluble and fat-soluble antioxidants, respectively, in the plasma of a healthy individual before, 4 hours after and 20 hours after vitamin use. The only antioxidants which show significant increases in plasma after vitamin administration are α-tocopherol at 20 hours and ascorbic acid at both 4 and 20 hours. This indicates that most of the ingested vitamins are taken up by cells and/or are excreted.

TABLE 4

Plasma water-soluble antioxidant levels before and after vitamin use
Mean ± SD of 10 healthy controls

| ANTIOXIDANT | 0 hours | 4 hours | 20 hours |
|---|---|---|---|
| Ascorbic acid | 10320 ± 1700 | 12480 ± 1900 | 16683 ± 2176 |
| GSSG | 17790 ± 6080 | 18640 ± 5070 | 16820 ± 5990 |
| GSH | 25880 ± 9650 | 24060 ± 8470 | 23980 ± 7660 |

TABLE 5

Plasma fat-soluble antioxidant levels before and after vitamin use
Mean ± SD of 10 healthy controls

| ANTIOXIDANT | 0 hours | 4 hours | 20 hours |
|---|---|---|---|
| α-tocopherol | 7460 ± 1820 | 7892 ± 1653 | 9320 ± 1941 |
| γ-tocopherol | 1672 ± 186 | 1743 ± 218 | 1856 ± 209 |
| lycopene | 248 ± 97 | 239 ± 103 | 299 ± 97 |
| α-carotene | 133 ± 80 | 132 ± 70 | 136 ± 71 |
| β-carotene | 437 ± 42 | 428 ± 87 | 448 ± 77 |
| coenzyme $Q_{10}$ | 297 ± 81 | 306 ± 86 | 319 ± 96 |

Figure 4:
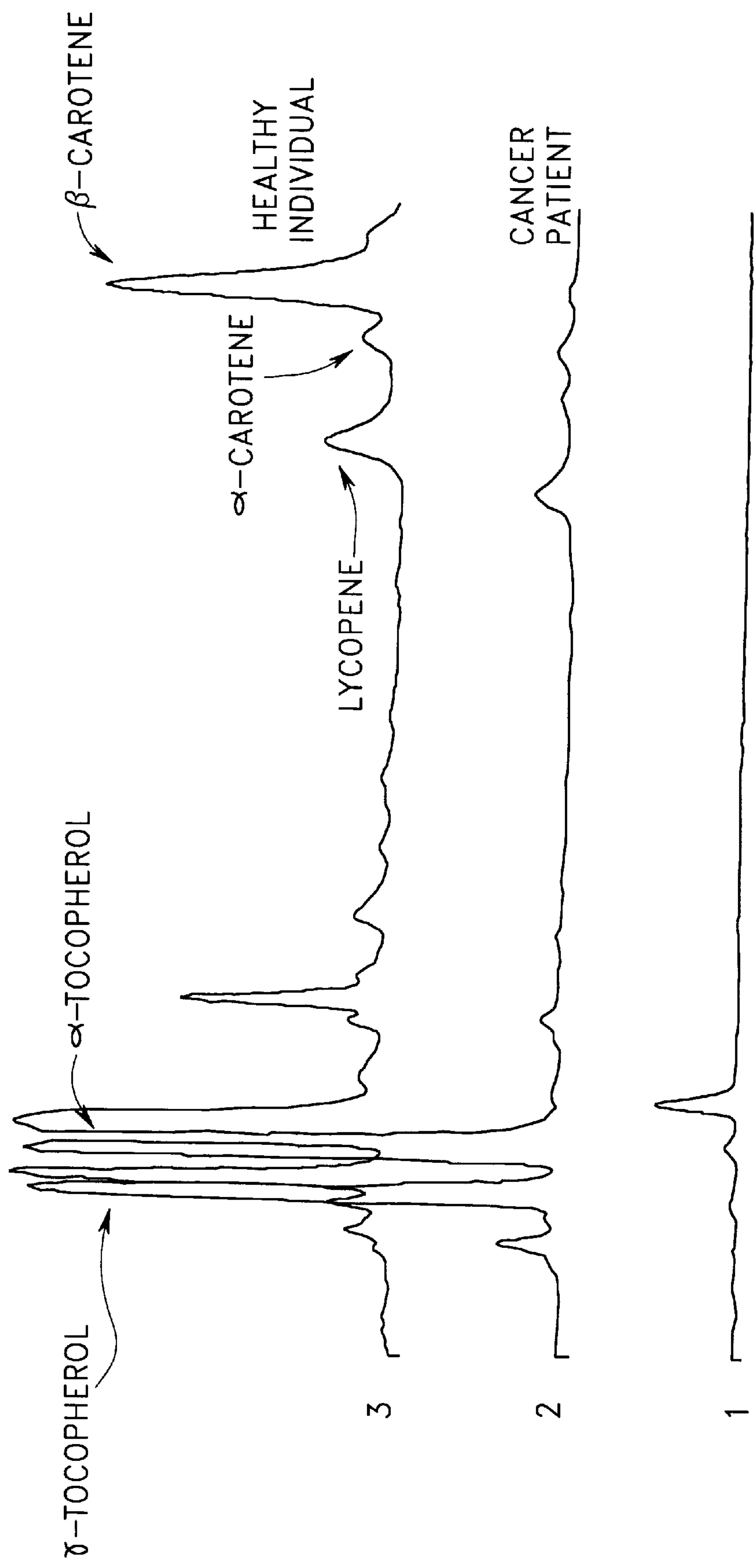
FIG. 4 is a chromatogram comparing levels of fat-soluble antioxidants in PBMC from a healthy individual and a cancer patient
Figure 5:
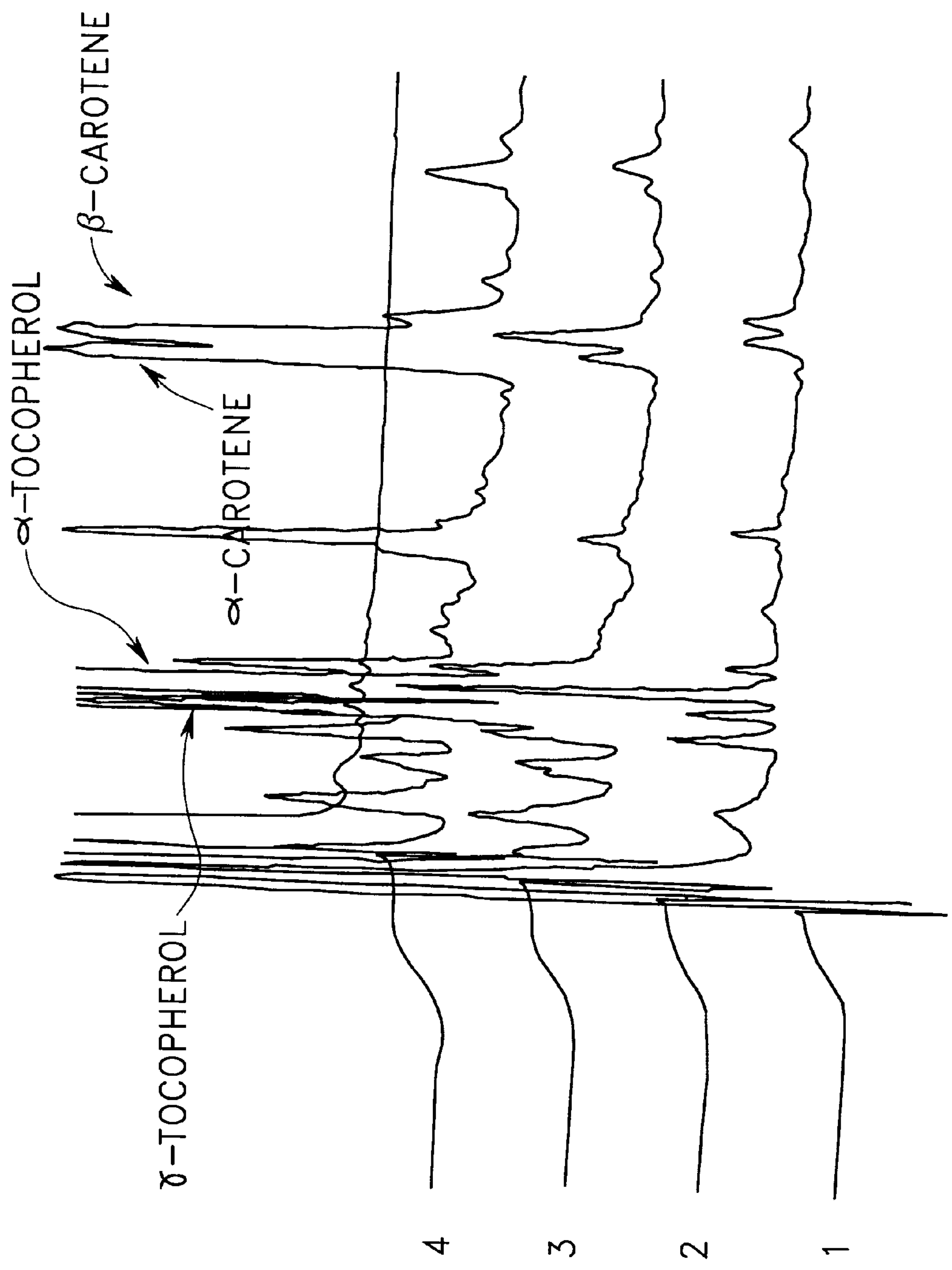
FIG. 5 is a chromatogram comparing plasma levels of various fat-soluble antioxidants in a healthy individual (top line) and two cancer patients.

FIGS. 4 and 5 show intracellular and plasma levels, respectively, of fat-soluble antioxidants in healthy individuals and cancer patients. As shown in FIG. 4 and 5 most fat-soluble antioxidant levels were significantly lower in PBMC from cancer patients compared to a healthy individual.

Blood samples were obtained from 10 breast cancer patients and 10 healthy control individuals. PBMC were isolated as described in Example 1 and antioxidant levels were determined as described in Examples 2 and 3. The results for plasma and intracellular water-soluble antioxidant levels (in ng/mL and ng/$3\times10^7$ PBMC, respectively) are shown in Tables 6 and 7, respectively.

TABLE 6

Plasma water-soluble antioxidant levels in healthy individuals and breast cancer patients

| Antioxidant | Healthy Controls | Breast Cancer Patients | % Decrease |
|---|---|---|---|
| Ascorbic acid | 9275 ± 2150 | 7123 ± 2272 | 23 |
| GSSG | 18410 ± 5030 | 14260 ± 2180 | 23 |
| GSH | 26730 ± 11050 | 5860 ± 2165 | 78 |

TABLE 7

Intracellular water-soluble antioxidant levels in healthy individuals and cancer patients

| Antioxidant | Healthy Controls | Breast Cancer Patients | % Decrease |
|---|---|---|---|
| Ascorbic acid | 6327 ± 2245 | 4118 ± 1670 | 35 |
| GSSG | 38530 ± 16780 | 34690 ± 12490 | 10 |
| GSH | 48530 ± 16780 | 31090 ± 14550 | 36 |

As determined from the values presented in Table 6, plasma ascorbic acid, GSSG and GSH levels were 23%, 23%, and 78% lower, respectively, in breast cancer patients compared to healthy control individuals. As determined from the values presented in Table 7, intracellular ascorbic acid, GSSG and GSH levels were 35%, 10%, and 36% lower, respectively, in breast cancer patients compared to healthy control individuals.

The results for plasma and intracellular fat-soluble antioxidant levels (in ng/mL and ng/$3\times10^7$ PBMC, respectively) are shown in Tables 8 and 9, respectively.

TABLE 8

Plasma fat-soluble antioxidant levels in healthy individuals and cancer patients

| Antioxidant | Healthy Controls | Breast Cancer Patients | % Decrease |
|---|---|---|---|
| α-tocopherol | 8500 ± 2000 | 5200 ± 1700 | 39 |
| γ-tocopherol | 1780 ± 160 | 1460 ± 210 | 18 |
| lycopene | 235 ± 84 | 132 ± 67 | 44 |
| α-carotene | 129 ± 70 | 81 ± 30 | 38 |
| β-carotene | 427 ± 81 | 328 ± 92 | 23 |
| Coenzyme $Q_{10}$ | 285 ± 47 | 183 ± 43 | 36 |

TABLE 9

Intracellular fat-soluble antioxidant levels in healthy individuals and cancer patients

| Antioxidant | Healthy Controls | Breast Cancer Patients | % Decrease |
|---|---|---|---|
| α-tocopherol | 3160 ± 974 | 2075 ± 633 | 34 |
| γ-tocopherol | 528 ± 319 | 403 ± 186 | 24 |
| lycopene | 109 ± 22 | 38 ± 23 | 65 |
| α-carotene | 16 ± 9 | 6 ± 5 | 62 |
| β-carotene | 73 ± 31 | 28 ± 11 | 62 |
| Coenzyme $Q_{10}$ | 192 ± 47 | 67 ± 26 | 65 |

As determined from the values presented in Table 8, plasma α-tocopherol, γ-tocopherol, lycopene, α-carotene, β-carotene and coenzyme $Q_{10}$ levels were 39%, 18%, 44%, 37%, 23%, and 36% lower, respectively, in breast cancer patients compared to healthy control individuals. As determined from the values presented in Table 9, intracellular levels of α-tocopherol, γ-tocopherol, lycopene, α-carotene, β-carotene and coenzyme $Q_{10}$ levels were 34%, 24%, 65%, 62%, 62%, and 65% lower, respectively, in breast cancer patients compared to healthy control individuals.

The ratio of intracellular to plasma levels of antioxidants is also an indication of the overall oxidative health of an individual In a preferred embodiment, this ratio is about 1.0 which indicates that significant intracellular uptake has occurred. In a more preferred embodiment, this ratio is greater than 1.0, which indicates that antioxidant uptake from the blood into the PBMCs is very efficient and that more antioxidants are inside the cell where they can exert their beneficial effects. Thus, these ratios can also be used to determine whether an individual should take additional precautionary measures such as increasing their intake of antioxidants.

The above detailed description of the invention is set forth solely to assist in understanding the invention. It is to be understood that variations of the invention, including all equivalents now known or later developed, are to be considered as falling within the scope of the invention, which is limited only by the following claims.

What is claimed is:

1. A method for determining whether a test individual requires an an increase in precautionary measures to lower the risk of developing cancer, comprising the steps of:

obtaining a median control level of one or more antioxidants present in peripheral blood mononuclear cells (PBMC) taken from healthy individuals who do not have cancer;

isolating PBMC from said test individual;

determining the level of said one or more antioxidants present in said PBMC by high performance liquid chromatography (HPLC);

comparing said level of said one or more antioxidants to said median control level of said one or more antioxidants, wherein a decrease in said level of said one or more antioxidants compared to said control level indicates that an increase in precautionary measures is required; and taking one or more precautionary measures to prevent the development of cancer in the test individual when required.

2. The method of claim 1, wherein said one or more antioxidants are water-soluble.

3. The method of claim 2, wherein said one or more water-soluble antioxidants are selected from the group consisting of ascorbic acid, oxidized glutathione, reduced glutathione, cysteine and uric acid.

4. The method of claim 1, wherein said one or more antioxidants are fat-soluble.

5. The method of claim 4, wherein said one or more fat-soluble antioxidants are selected from the group consisting of α-carotene, β-carotene, lycopene, α-tocopherol, γ-tocopherol, retinol, lutein, zeaxanthin, cryptoxanthin and coenzyme $Q_{10}$.

6. The method of claim 1, wherein said antioxidants are a combination of water-soluble and fat-soluble antioxidants.

7. The method of claim 1, wherein said precautionary measures are selected from the group consisting of increased intake of one or more antioxidants, increased exercise, a change in environment, decreased dietary fat intake and decreased exposure to chemicals.

* * * * *